United States Patent
Xing et al.

(10) Patent No.: US 9,446,083 B2
(45) Date of Patent: Sep. 20, 2016

(54) FATTY ACID COMPOSITION AND PLANT EXTRACT AND PHARMACEUTICAL PREPARATION AND APPLICATION THEREOF

(76) Inventors: Junwu Xing, Shandong (CN); Ning Qu, Shandong (CN); Yiqian Xing, Shandong (CN)

( * ) Notice: Subject to any disclaimer, the term of this patent is extended or adjusted under 35 U.S.C. 154(b) by 47 days.

(21) Appl. No.: 14/129,803

(22) PCT Filed: Jun. 25, 2012

(86) PCT No.: PCT/CN2012/077432
§ 371 (c)(1),
(2), (4) Date: May 27, 2014

(87) PCT Pub. No.: WO2013/000382
PCT Pub. Date: Jan. 3, 2013

(65) Prior Publication Data
US 2014/0287076 A1    Sep. 25, 2014

(30) Foreign Application Priority Data

Jun. 29, 2011 (CN) .......................... 2011 1 0179692

(51) Int. Cl.
| | |
|---|---|
| *A01N 65/00* | (2009.01) |
| *A61K 36/21* | (2006.01) |
| *A61K 31/20* | (2006.01) |
| *A61K 31/201* | (2006.01) |
| *A61K 31/202* | (2006.01) |
| *A61K 8/37* | (2006.01) |
| *A61Q 17/00* | (2006.01) |
| *A61Q 17/04* | (2006.01) |
| *A61Q 19/00* | (2006.01) |
| *A61Q 19/10* | (2006.01) |
| *A61K 8/97* | (2006.01) |

(52) U.S. Cl.
CPC ................. *A61K 36/21* (2013.01); *A61K 8/37* (2013.01); *A61K 8/97* (2013.01); *A61K 31/20* (2013.01); *A61K 31/201* (2013.01); *A61K 31/202* (2013.01); *A61Q 17/00* (2013.01); *A61Q 17/04* (2013.01); *A61Q 19/00* (2013.01); *A61Q 19/005* (2013.01); *A61Q 19/007* (2013.01); *A61Q 19/10* (2013.01)

(58) Field of Classification Search
CPC .................................................... A61K 36/00
USPC ......................................................... 424/725
See application file for complete search history.

(56) References Cited

FOREIGN PATENT DOCUMENTS

| CN | 1057191 A | 12/1991 |
|---|---|---|
| EP | 2 343 044 A1 | 7/2011 |
| WO | 2010/037882 A1 | 4/2010 |

OTHER PUBLICATIONS

Liu et al., Extraction of Suaeda Salsa Seed Oil by Supercritical CO2 and its Analysis by GC/MS, China Oils and Fats, vol. 28, No. 2, pp. 42-45 (2003) (English abstract provided).
Li et al., Extraction and Characteristics Analysis of Suaeda Salsa Seed Oil, China Oils and Fats, vol. 35, No. 1, pp. 74-76 (2010) (English abstract provided).
Louw, The Keloid Phenomenon: Progress Toward a Solution, Clinical Anatomy, vol. 20, pp. 3-14 (2007).
Cheng et al., Fat and Wound Healing, Infect. inflamm. Rep., vol. 4, No. 2, pp. 122-124 (Jun. 2003) (English abstract provided).
Ji et al., The Prospect of Development and Utilization of Halophyte Resources, China Food and Nutrition, No. 4, pp. 25-26 (2004) (English abstract provided).
Bonin et al., The Topical Protective Effect of Soybean-Germ Oil Against UVB-Induced Cutaneous Erythema: An In Vivo Evaluation, Arch. Pharm. Chem. Life Sci., vol. 338, No. 12, pp. 598-601 (2005) (English abstract provided).
Zheng et al., Chemical Composition and Anti-Inflammation of Methanol/Chloroform Extracts from Seeds and Seedlings of Suaeda Salsa (L.) Pall, Chinese Traditional Patent Medicine, vol. 25, No. 12, pp. 997-1002 (2003) (English abstract provided).
Zhi et al., Observation on the Effect of Recombinant Epidermal Growth Factor on Grade II Trauma, China Tropical Medicine, vol. 7, pp. 70-71 (2007) (English abstract provided).
Clinical Application of Recombinant Human Epidermal Growth Factor in Wound Healing, Qinghai Medical Journal, vol. 34, No. 11, pp. 61-62 (2004) (English abstract provided).
Al-Ani et al., "Effect of Suaeda aegyptiaca Extracts on Some Microorganisms In vivo and In vitro." Journal of Biology & Life Sciences, 2011, 2(1):16-21.
Ravikumar et al., "Hepatoprotective and antioxidant properties of Suaeda maritima (L.) Dumort ethanolic extract on concanavalin-A induced hepatotoxicity in rats," Indian Journal of Experimental Biology, vol. 49, Jun. 2011, pp. 455-460.
Hu et al., "Experimental Study on Resistant Action of Huangxucai Oil to Atherosclerosis and Aging; I. Experimental Study on Resistant Action of Huangxucai Oil to Atherosclerosis," (1992), 30(3), 190-194 and 197. Chemical Abstracts Accession No. 1993:52135.
Li et al., "Experimental Study on Resistant Action of Huangxucai Oil to Atherosclerosis and Aging:II. Study on Nutritional Composition of the Huangxucai Seed." (1992), 30(3), 195-198, Chemical Abstracts Accession No. 1993:35965.

*Primary Examiner* — Michael Meller
(74) *Attorney, Agent, or Firm* — Volpe and Koenig, P.C.

(57) ABSTRACT

A fatty acid composition containing linoleic acid, linolenic acid and oleic acid is provided. Also provided is a fatty acid composition containing linoleic acid, linolenic acid and oleic acid, and at least one selected from palmitinic acid, palmitoleic acid, stearic acid, arachidic acid and docosanoic acid. A plant extract and a pharmaceutical preparation are provided, wherein the pharmaceutical preparation contains an active component including at least one of the fatty acid composition, the plant extract and modified products thereof. Also provided is an application of the fatty acid composition, the plant extract and the pharmaceutical preparation in multiple fields. The pharmaceutical preparation may function to repair various wounds and traumas in skin, mucosa, lumina and muscular tissues.

19 Claims, No Drawings

FATTY ACID COMPOSITION AND PLANT EXTRACT AND PHARMACEUTICAL PREPARATION AND APPLICATION THEREOF

FIELD OF THE INVENTION

The present invention relates to plant extract, fatty acid composition and pharmaceutical preparation, and their application in multiple fields.

BACKGROUND OF THE INVENTION

Various traumas of human and animals caused by different reasons happen every day. There is a wide range of social demand for research and development of high-performance trauma treatment medicines. At present, the clinical medicines for treatment of trauma mainly include various kinds of growth factors, such as: epidermal growth factor (EGF), basic fibroblast growth factor (FGF) and platelet derived growth factor (PDGF), as well as compound preparations of traditional Chinese medicine and Western medicine, such as: sterilizing and antibiotic preparations (Observation on Medicinal Effect of EGF Solution in Treating Degree-II Skin Trauma, China Tropical Medicine, Vol 7, 2007, Page 70-71; Progress of Clinical Application of Recombinant Human Epidermal Growth Factor in Healing of Wounds, Qinghai Medical Journal, 2004, Vol 34, Issue 11, Page 61-62).

However, the above medicines for treatment of trauma all have respective inherent limitations in clinical application. For example, EGF shows a good curative effect on superficial skin injury, but it has a poor curative effect on wounds of above degree II and even no effect on the treatment of refractory wounds. Traditional Chinese medicine Yunnan Baiyao type preparations are applicable to stopping bleeding and pain, but their effect in repairing and treating deep wounds is not desirable and it is liable to scab of wounds, purulence and infection under scars and difficult healing of wounds. Furthermore, the effect of these preparations is not desirable in treating burn and scald. In comparison, traditional Chinese medicine burn cream preparations have a good curative effect on ordinary burn and scald, but their curative effect on serious burn and scald of above degree II is poor. Furthermore, the effect of these preparations is not desirable in treating wounds not caused by burn or scald. Other compound preparations of Western medicine are mostly antibiotic compound compositions for blood coagulation and pain relief and have certain effect in preventing wound infection and stopping bleeding and pain, but they don't have a direct effect on the healing of wounds. Band-aid trauma preparations are only suitable to bonding of the surface of a small incised wound and cannot be used to treat a large-area wound and are not suitable to the treatment of non-incision wounds, such as: frictional injury, corrosive injury and burn injury.

SUMMARY OF THE INVENTION

The object of the present invention is to provide a new type of plant extract, fatty acid composition and pharmaceutical preparation that can effectively treat and repair various kinds of traumatic injuries, as well as the application of the foregoing extract, composition and pharmaceutical preparation in multiple fields.

The plants described in the present invention relate to the species of Chenopodiaceae *Suaeda* Forsk.ex Scop. This genus has more than 100 species of plants. They are distributed on coasts, deserts, lakeside and saline and alkaline land all over the world. More than 20 of them are found in China and grow in Xinjiang, Tibet, Northeast, Northwest, North China, Central China and coastal provinces (Xing Junwu, Saline and Alkaline Environment and Grain Crisis, Qingdao Ocean University Press, 1993). No medical application of the plants under this genus was recorded in the past. The *Roots and Herbs for Disaster Relief* written in the Ming Dynasty of China first recorded the morphological characteristics, growth environment and specific edible method of *S. glauca* Bge. under this genus as edible potherb and indicated its non-toxicity. *The Dictionary of Chinese Herbs* included it in 1986 (Dictionary of Chinese Herbs, Shanghai Science and Technology Publishing House, 1986), but it just continued to cite the descriptions of the *Roots and Herbs for Disaster Relief* and subsequent ancient literature on "non-toxicity", "the leaves are slightly salty in taste and slightly cold in nature", "clearing heat and removing obstruction" and edible methods as well as plant taxonomy, morphology and existent environment and didn't record concrete medical application. Since Xing Junwu initiated crop research of *S. glauca* Bge. last century, the researches on the utilization of *Suaeda. Salsa* (L.) Pall. have been increasing, but they mostly concentrate on functional food, for example in such aspects as health care, slimming or improvement of blood fat. The research on clinical medical application and its indications is still a blank. For this reason, the inventor of the present invention has made in-depth research on the indications of *Suaeda* in clinical medical application and consequently completed the present invention.

The present invention provides a *Suaeda* extract. Preferably, the plant extract is the extract of *Suaeda* seeds.

The *Suaeda* extract described in the present invention includes without limitation: at least one of *Suaeda. Salsa* (L.) Pall. extract, *S. glauca* Bge. extract, *S. corniculata* (C.A. Mey) Bunge extract and *S. prostrata* Pall. extract.

The present invention provides a fatty acid composition, wherein the composition contains linoleic acid, linolenic acid and oleic acid.

The present invention also provides a fatty acid composition, wherein the composition contains linoleic acid, linolenic acid and oleic acid, as well as at least one of palmitic acid, palmitoleic acid, stearic acid, arachidic acid and docosanoic acid.

The present invention also provides a pharmaceutical preparation, containing active components, wherein the active components include at least one of the foregoing fatty acid composition, the foregoing plant extract and the modified product of the plant extract.

Further, the present invention also provides a plurality of usages of the foregoing plant extract, the foregoing fatty acid composition and the foregoing pharmaceutical preparation. To be specific, the present invention provides the application of at least one of the foregoing plant extract, the foregoing fatty acid composition and the foregoing pharmaceutical preparation in preparing medicines for treatment of external trauma and internal injury.

The present invention provides the application of at least one of the foregoing plant extract, the foregoing fatty acid composition and the foregoing pharmaceutical preparation in preparing medicines for treatment of burn and scald, or nerve injury caused by various kinds of trauma.

The present invention provides the application of at least one of the foregoing plant extract, the foregoing fatty acid composition and the foregoing pharmaceutical preparation in preparing medicines for repair of tissue ulceration or necrosis.

The present invention provides the application of at least one of the foregoing plant extract, the foregoing fatty acid composition and the foregoing pharmaceutical preparation in preparing medicines for repair of trauma.

The present invention provides the application of at least one of the foregoing plant extract, the foregoing fatty acid composition and the foregoing pharmaceutical preparation in preparing cosmetics.

The foregoing plant extract and fatty acid composition provided by the present invention may be used both externally and internally and have no toxic side effects, no irritation and no adverse reaction.

The pharmaceutical preparation related to the present invention has an efficacy of clearing heat, stopping pain, generating muscle, diminishing swelling, relieving internal heat or fever and preventing rot and has a function of repairing the injuries of skin and muscle tissues, lumen, mucosa tissue and nervous tissue. When it is used to repair and treat various kinds of trauma, it has the advantages of rapid healing, no infection, no scar and no formation of purulent tissue, can effectively eliminate tissue exudate, wipe off the inflammation and infection induced by trauma and promote repair and treatment of muscle, skin mucosa, nerve and other tissues at the traumatic locations, and is particularly applicable to the repair and healing of various kinds of refractory traumas.

DETAILED DESCRIPTION OF THE EMBODIMENTS

The present invention provides a plant extract, wherein the plant extract is *Suaeda* extract. Preferably, the *Suaeda* extract is at least one of *Suaeda. Salsa* (L.) Pall. extract, *S. glauca* Bge. extract, *S. corniculata* (C.A. Mey) Bunge extract and *S. prostrata* Pall. extract. *Suaeda* plants have similar chemical composition, so they have similar bioactivity. For example, if based on the weight of seed extract, the fatty acids in *S. glauca* Bge. seeds and their contents are: palmitic acid 9.36 wt %, palmitoleic acid 0.53 wt %, stearic acid 2.07 wt %, oleic acid 12.48 wt %, linoleic acid 63.22 wt %, arachidic acid 0.95 wt %, linolenic acid 7.89 wt %, myristic acid 0.28 wt %, eicosapentaenoic acid 0.73 wt % and docosahexaenoic acid 0.02 wt %. If based on the weight of seed extract, the fatty acids in *S. corniculata* (C.A. Mey) Bunge seeds and their contents are: palmitic acid 11.01 wt %, palmitoleic acid 1.02 wt %, stearic acid 2.18 wt %, oleic acid 13.12 wt %, linoleic acid 65.23 wt %, arachidic acid 0.86 wt %, linolenic acid 6.54 wt % and myristic acid 0.04 wt %.

According to the present invention, the preferred *Suaeda* extract is *Suaeda* seed extract, the more preferred *Suaeda* extract is *Suaeda. salsa* (L.) Pall. seed extract or *S. glauca* Bge. seed extract, the further more preferred is the extract of mature seeds of *Suaeda. Salsa* (L.) Pall. or *S. glauca* Bge. and the most preferred is the extract of mature seeds of *Suaeda. Salsa* (L.) Pall. According to the present invention, the mature seeds of *Suaeda. Salsa* (L.) Pall. and *S. glauca* Bge. may be obtained by picking in the wild or by artificial breeding. All the obtaining methods are known to those skilled in the art.

According to the present invention, preferably, if based on the weight of plant extract, the plant extract contains: 8-18 wt % oleic acid, 20-85 wt % linoleic acid, 1-35 wt % linolenic acid (linolenic acid may be α-linolenic acid or γ-linolenic acid, or both), 3-15 wt % palmitic acid, 0.5-5 wt % palmitoleic acid, 0.5-5 wt % stearic acid, 0.1-3 wt % arachidic acid and 0.01-0.5 wt % docosanoic acid.

In a preferred embodiment, if based on the weight of plant extract, the plant extract contains: 8-18 wt % oleic acid, 60-82 wt % linoleic acid, 2-10 wt % linolenic acid, 6-12 wt % palmitic acid, 0.5-2 wt % palmitoleic acid, 0.5-3 wt % stearic acid, 0.5-1 wt % arachidic acid and 0.2-0.5 wt % docosanoic acid.

In another preferred embodiment, if based on the weight of plant extract, the plant extract contains: 8-18 wt % oleic acid, 70-82 wt % linoleic acid, 2-10 wt % linolenic acid, 3-8 wt % palmitic acid, 0.5-3 wt % palmitoleic acid, 0.5-3 wt % stearic acid, 0.1-1 wt % arachidic acid and 0.01-0.5 wt % docosanoic acid.

Further preferably, if based on the weight of plant extract, the plant extract contains: 8-15 wt % oleic acid, 60-80 wt % linoleic acid, 2-10 wt % linolenic acid, 3-10 wt % palmitic acid, 0.5-3 wt % palmitoleic acid, 0.5-3 wt % stearic acid, 0.1-1 wt % arachidic acid and 0.01-0.5 wt % docosanoic acid.

Or further preferably, if based on the weight of plant extract, the plant extract contains: 8-15 wt % oleic acid, 72-80 wt % linoleic acid, 2-6 wt % linolenic acid, 3-8 wt % palmitic acid, 0.5-3 wt % palmitoleic acid, 0.5-3 wt % stearic acid, 0.1-1 wt % arachidic acid and 0.01-0.5 wt % docosanoic acid.

More preferably, if based on the weight of plant extract, the plant extract contains: 10-13 wt % oleic acid, 60-76 wt % linoleic acid, 3-8 wt % linolenic acid, 6-10 wt % palmitic acid, 0.5-1.5 wt % palmitoleic acid, 1-2.1 wt % stearic acid, 0.5-1 wt % arachidic acid and 0.2-0.4 wt % docosanoic acid.

Or more preferably, if based on the weight of plant extract, the plant extract contains: 9-11 wt % oleic acid, 74-76 wt % linoleic acid, 4-5 wt % linolenic acid, 6-8 wt % palmitic acid, 1-2 wt % palmitoleic acid, 1-2 wt % stearic acid, and 0.5-0.8 wt % arachidic acid and 0.2-0.4 wt % docosanoic acid.

According to the present invention, the plant extract is a concept well known in the art. It is a product which consists of one or a plurality of active components concentrated and obtained from a plant by method of physical and chemical extraction and separation, without changing the structure of the active components. In the present invention, the method to obtain the plant extract may be a conventional method in the art as long as the composition of the obtained plant extract meets the foregoing requirements. For example, the method to obtain the plant extract may be at least one of compression method, leaching method, supercritical extraction method and water extraction method.

The compression method is a physical method by which the plant is pressed by mechanical force. The pressing device may be a device of hydraulic pressure, screw extrusion or other pressure. The compression method may be hot compression method or cold compression method.

The leaching method is a method well known in the art. It is a method by which an organic solvent is used as a leach liquor to extract fat from oil plant. In the present invention, the preferred leach liquor used in the leaching method is a solvent with a low boiling point. To be specific, a solvent with a boiling point of 40-90° C. is preferred and a solvent with a boiling point of 50-90° C. is more preferred. The leach liquor may be at least one of 6# solvent oil, n-hexane, benzene, dichloroethane, trichloroethylene and gasoline. In the present invention, the preferred leach liquor is food-grade solvent 6# solvent oil.

The supercritical extraction method (or called as supercritical fluid extraction method) is a technology in which a supercritical fluid is used as a solvent to extract and separate active components from solid or liquid. There are many gases can be used as supercritical fluids (extractants), such as: carbon dioxide, ethylene, ammonia, nitrous oxide and dichlorodifluoromethane etc. Typically, carbon dioxide is used as an extractant in supercritical extraction method.

The water extraction method refers to a method by which water replaces oil in oil plant to obtain fat. Without compression by pressure or extraction by solvent, the affinity of water with protein is greater than the affinity of oil with protein under a specific condition, so water infiltrates into oil plant to replace fat.

All of the foregoing methods are well known to those skilled in the art, so their conditions and concrete operation are not described here.

The present invention also provides a fatty acid composition, wherein the composition contains linoleic acid, linolenic acid and oleic acid.

The inventor of the present invention has discovered that the contents of linoleic acid, linolenic acid and oleic acid in the composition may vary in a very large range.

Preferably, if based on the weight of the composition, then in the composition, the content of oleic acid (structural formula: $CH_3(CH_2)_7CH\!=\!CH(CH_2)_7COOH$) is 0.5-99 wt %, the content of linoleic acid (structural formula: $CH_3(CH_2)_4(CH\!=\!CHCH_2)_2(CH_2)_6COOH$) is 0.5-99 wt %, and the content of linolenic acid (structural formula: $CH_3CH_2(CH\!=\!CHCH_2)_3(CH_2)_6COOH$) is 0.5-99 wt %; more preferably, if based on the weight of the composition, then in the composition, the content of oleic acid is 5-30 wt %, the content of linoleic acid is 60-90 wt %, and the content of linolenic acid is 0.5-30 wt %; further more preferably, if based on the weight of the composition, then in the composition, the content of oleic acid is 6-20 wt %, the content of linoleic acid is 70-85 wt %, and the content of linolenic acid is 1-20 wt %; most preferably, if based on the weight of the composition, then in the composition, the content of oleic acid is 8-18 wt %, the content of linoleic acid is 70-82 wt %, and the content of linolenic acid is 2-12 wt %, preferably 2-10 wt %.

More preferably, the composition consists of linoleic acid, linolenic acid and oleic acid in the foregoing ranges of content.

The present invention also provides a fatty acid composition, wherein the composition contains linoleic acid, linolenic acid and oleic acid, as well as at least one selected from palmitic acid, palmitoleic acid, stearic acid, arachidic acid and docosanoic acid.

According to the present invention, preferably, if based on the weight of the composition, then in the composition, the content of oleic acid is 0.5-95 wt %, more preferably 6-20 wt %, further more preferably 8-18 wt % and most preferably 8-15 wt %; the content of linoleic acid is 0.5-95 wt %, more preferably 70-85 wt %, further more preferably 70-82 wt % and most preferably 72-80 wt %; the content of linolenic acid is 0.5-95 wt %, more preferably 1-20 wt %, further more preferably 2-10 wt % and most preferably 2-6 wt %; further, the preferred content of palmitic acid (structural formula: $CH_3(CH_2)_{14}COOH$) is 0-8 wt %, the preferred content of palmitoleic acid (structural formula: $CH_3(CH_2)_5CH\!=\!CH(CH_2)_7COOH$) is 0-3 wt %, the preferred content of stearic acid (structural formula: $CH_3(CH_2)_{16}COOH$) is 0-3 wt %, the preferred content of arachidic acid (structural formula: $CH_3(CH_2)_{18}COOH$) is 0-1 wt % and the preferred content of docosanoic acid (structural formula: $CH_3(CH_2)_{20}COOH$) is 0-1 wt % and the preferred total content of palmitic acid, palmitoleic acid, stearic acid, arachidic acid and docosanoic acid is 4-16 wt %.

Compared with the fatty acid composition not containing at least one selected from palmitic acid, palmitoleic acid, stearic acid, arachidic acid and docosanoic acid, the fatty acid composition containing at least one selected from palmitic acid, palmitoleic acid, stearic acid, arachidic acid and docosanoic acid is more stable and has a better clinical treatment effect, so it is preferred that the fatty acid composition provided by the present invention contains at least one selected from palmitic acid, palmitoleic acid, stearic acid, arachidic acid and docosanoic acid.

According to the fatty acid composition provided by the present invention, when the fatty acid composition contains palmitic acid, it is more stable and has a better clinical treatment effect, so it is preferred that the fatty acid composition provided by the present invention contains palmitic acid and preferably, the content of palmitic acid is 3-8 wt % based on the total amount of the composition.

According to the fatty acid composition provided by the present invention, when the fatty acid composition contains palmitoleic acid, it is more stable and has a better clinical treatment effect, so it is preferred that the fatty acid composition provided by the present invention contains palmitoleic acid and preferably, the content of palmitoleic acid is 0.5-3 wt % based on the total amount of the composition.

According to the fatty acid composition provided by the present invention, when the fatty acid composition contains stearic acid, it is more stable and has a better clinical treatment effect, so it is preferred that the fatty acid composition provided by the present invention contains stearic acid and preferably, the content of stearic acid is 0.5-3 wt % based on the total amount of the composition.

According to the fatty acid composition provided by the present invention, when the fatty acid composition contains arachidic acid, it is more stable and has a better clinical treatment effect, so it is preferred that the fatty acid composition provided by the present invention contains arachidic acid and preferably, the content of arachidic acid is 0.1-1 wt % based on the total amount of the composition.

According to the fatty acid composition provided by the present invention, when the fatty acid composition contains docosanoic acid, it is more stable and has a better clinical treatment effect, so it is preferred that the fatty acid composition provided by the present invention contains docosanoic acid and preferably, the content of docosanoic acid is 0.01-0.5 wt % based on the total amount of the composition.

More preferably, the composition contains oleic acid, linoleic acid, linolenic acid, palmitic acid, palmitoleic acid, stearic acid, arachidic acid and docosanoic acid, accounting for 95-100 wt % of the composition. Most preferably, the composition consists of oleic acid, linoleic acid, linolenic acid, palmitic acid, palmitoleic acid, stearic acid, arachidic acid and docosanoic acid.

The foregoing composition may be obtained by mixing all components in the foregoing proportion, or may be directly extracted from natural plant material which for example may be the foregoing *Suaeda*, including but not limited to: at least one of *Suaeda. Salsa* (L.) Pall., *S. glauca* Bge., *S. corniculata* (C.A.Mey) Bunge and *S. prostrata* Pall. All the components are compounds well known in the art and may be obtained by various methods, for example: commercial purchase, artificial synthesis, and extraction from natural plant materials.

On the basis of the foregoing invention, the present invention further provides a pharmaceutical preparation, containing active components, wherein the active components include at least one of the foregoing fatty acid composition, the foregoing plant extract and the modified product of the plant extract. The modified product of the plant extract is a concept well known in the art. In other words, it is a product, such as: solid or semisolid product, obtained from treatment of the plant extract by a method well known to those skilled in the art, such as: chemical combination, hydrogenation or conjugation. Further, the active components may also include the products obtained from deep processing of the foregoing plant extract by other conventional means in the art.

In the present invention, the pharmaceutical preparation may only use the foregoing fatty acid composition, plant extract and the modified product of the plant extract as active components, or the pharmaceutical preparation may also be a compound preparation. The concept of compound preparation is well known in the art, i.e.: it is a mixed preparation of two or more than two medicines and may be a mixed preparation of traditional Chinese medicines, or Western medicines, or traditional Chinese medicines and Western medicines. The present invention does not have particular limitation to the types and dosages of other drugs in the compound preparation. They may be used according to the current usage and dosages of the drugs (including the cases of separate use and use as compound preparations).

When the pharmaceutical preparation only uses the foregoing fatty acid composition, plant extract and the modified product of the plant extract as active components, preferably, if based on the weight of the pharmaceutical preparation, then in the pharmaceutical preparation, the content of active components is 1-100 wt % and the rest are pharmaceutical adjuvants. For example, the content of active components in the active preparation may be 10 wt %, 20 wt %, 30 wt %, 40 wt %, 50 wt %, 55 wt %, 60 wt %, 65 wt %, 70 wt %, 75 wt %, 80 wt %, 85 wt %, 90 wt %, 95 wt %, 98 wt % or 99 wt %. The content of active components in the pharmaceutical preparation has a relation with the dosage form of the pharmaceutical preparation. Those skilled in the art can select appropriate content of active components based on dosage form. When the pharmaceutical preparation is a compound preparation, the dosages of the foregoing fatty acid composition, the foregoing plant extract and the modified product of the plant extract in the pharmaceutical preparation may be same as the abovementioned or may be adjusted appropriately based on the types of other drugs used in the compound preparation.

The pharmaceutical adjuvants are various kinds of pharmaceutical adjuvants in the art, including but not limited to: at least one of tartaric acid, malic acid, Arabic gum, Aspartame, carnauba wax, white vaseline, white beeswax, β-cyclodextrin, propylene glycol, Poloxamer, entersoluble gelatin or various kinds of animal or plant-based vacant capsules, soft capsules, acetic acid, sodium acetate, soybean lecithin, cholesterol, yolk lecitin, starch, propyl p-hydroxybenzoate, methyl paraben, dimethicone, silica, titanium dioxide, fumaric acid, citric acid, magnesium aluminum silicate, pectin, fructose, sodium alginate, black iron oxide, purple iron oxide, brown iron oxide, red iron oxide, yellow iron oxide, dextrin, sodium cyclamate, vaseline, xanthan gum, mixed fatty glyceride, polyvinylpolypyrrolidone, Sodium cross-linked carboxymethyl cellulose, gelatin for capsule, sodium pyrosulfite, polysorbate 20, polysorbate 40, polysorbate 80, povidone K30, polyethylene glycol 400, polyethylene glycol 800, polyethylene glycol 1000, polyethylene glycol 1500, polyethylene glycol 4000, polyethylene glycol 6000, polyvinyl alcohol, diethyl phthalate, monopotassium phosphate, dipotassium phosphate, sodium hydrogen phosphate, thiomersal, sulfuric acid, calcium sulfate, maltodextrin, maltose, strong ammonia solution, propyl hydroxybenzoate, methyl hydroxybenzoate, ethyl hydroxybenzoate, hydroxypropyl-(3-cyclodextrin, sodium hydroxide, light magnesium oxide, light liquid paraffin, agar, lactose, chloretone, triethanolamine, sorbic acid, sorbitan monostearate (Span 60), sorbitan monooleate (Span 80), sorbitan monolaurate (Span 20), sorbitan monopalmitate (Span 40), sorbitan trioleate (Span 40), sodium dodecyl sulfonate, sodium carboxyl methyl starch, sodium carboxymethylcellulose, steviosin, anhydrous sodium sulfite, hydrochloric acid, diluted hydrochloric acid, lanolin, disodium edetate, cellulose acetate, ethyl acetate, isopropanol, polyoxyl (40) stearate, zein, various kinds of polysaccharide, saccharin and oligosaccharide, various kinds of protein and peptides components, pregelatinized starch, cane sugar and sucrose stearate.

According to the present invention, the pharmaceutical preparation may be made into various dosage forms applicable to different usage. For example, it may be made into various dosage forms for external use, including but not limited to: at least one of cream, paste, suppository, gauze, liniment, aerosol, powder and film, and may also be made into various dosage forms for internal use, including injection and various orally administered dosage forms, such as: at least one of capsule (hard capsule and soft capsule), solution, dispersant, emulsion, tablet and pill. When it is made into aerosol, it may be sprayed to the wounded part by pressure and is applicable to fast administration and treatment of wounds in a large area; the gauze is used to cover and treat a wound; by being mixed with various kinds of chitosan powder or cuttlebone powder or other traditional Chinese medicine or Western medicine powder and their adjuvants, it may be made into cream, which has the functions of stopping bleeding, resisting inflammation, etc.; when it is made into band-aid, it may be used to close the incision of a small fracture wound and properly fix the wound, thus making for healing; when it is made into suppository, it is used to treat lacerated wounds inside anus, etc.; when it is made into soft capsule liniment, it is handy and convenient for treatment of unexpected injury, or may be administered internally to treat injury of endothelium or blood vessel wall; when it is made into injection, it is used to treat injury of internal wall of organs, etc. When it is made into a needed dosage form, the pharmaceutical preparation contains adjuvants necessary for this dosage form. The preparation methods of the dosage forms are well known to those skilled in the art, so they are not described here.

Further, the plant extract and fatty acid composition provided by the present invention may be directly used as medicines. They are kept in bottles, bags or other ware. During use, cotton swab, cotton ball, writing brush, hairbrush, suction tube or other tools may be used to soak or suck them and smear them to the wounded parts so that the medicine fully covers the wounds.

The plant extract, fatty acid composition and pharmaceutical preparation provided by the present invention have various use, including but not limited to the following.

The present invention provides the application of at least one of the foregoing plant extract, fatty acid composition and pharmaceutical preparation in preparing medicines for treatment of external trauma and internal injury.

The external trauma refers to mechanical injury of skin and flesh caused by external force, including but not limited to: trauma caused by cutting, stabbing, chopping, laceration, friction, tearing, impact, fall or tumbling. The internal injury refers to non-epidermal injury inside body.

The present invention provides the application of at least one of the foregoing plant extract, fatty acid composition and pharmaceutical preparation in preparing medicines for treatment of burn and scald or nervous injury caused by various kinds of trauma.

In the present invention, the burn and scald may be the burn and scald caused by various reasons, such as: tissue injury caused by fire, electricity, (radioactive) radiation, UV light, high-temperature liquid, high-temperature gas, high-temperature solid, or chemical corrosive substances.

The present invention provides the application of at least one of the foregoing plant extract, fatty acid composition and pharmaceutical preparation in preparing medicines for repair of tissue ulceration or necrosis.

According to the present invention, the tissue ulceration or necrosis may include at least one of skin ulceration or necrosis, muscle ulceration or necrosis, mucosa ulceration or necrosis, and cavity ulceration or necrosis. For example, intractable ulcer caused by diabetes or varicosity, gangrene wound, bedsore and ulceration and bleeding of alimentary tract.

The present invention provides the application of at least one of the foregoing plant extract, fatty acid composition and pharmaceutical preparation in preparing medicines for repair of trauma.

According to the present invention, the trauma may include external injury and internal injury of human body, for example: the wounds resulting from surgery, external injection, intubation or puncture. The surgery includes plastic surgery for beauty, gynecological surgery, etc. Further, the repair of trauma may also include for example preoperative oral treatment and postoperative bleeding stopping and inflammation reduction of tooth extraction or dental filling, treatment of gingival hamorrhage, hemorrhinia, infection and hemorrhage of nasal mucosa, swelling and pain in throat, and inflammation of middle ear and external ear, as well as skin sterilization before intravenous or intramuscular injection and wound repair and healing after injection.

The present invention provides the application of at least one of the foregoing plant extract, fatty acid composition and pharmaceutical preparation in preparing cosmetics. The cosmetics refer to the chemical industrial products or fine chemical products spread to any location of human body surface, such as: skin, hair, nail, lip and tooth, by smearing, spray or other similar methods for the purpose of cleaning, care, beauty, embellishment, change of appearance, or correcting body odor, or maintaining a good condition. The cosmetics include without limitation cosmetics for cleaning, cosmetics for hair, general cosmetics, cosmetics for beauty and cosmetics for treatment and nursing.

More specifically, the plant extract, fatty acid composition and pharmaceutical preparation provided by the present invention may resist radiation hazard of ultraviolet light to human body, so they can be made into sunscreens and used to prevent and treat skin injury of the professionals engaged in water sports like sailing, swimming and diving. Further, the fatty acid composition, plant extract and pharmaceutical preparation provided by the present invention also have an effect of skin moisturizing, so they may be used to prepare anti-chapping preparations, skin moisturizing preparations and other skin care products. Further, they may also be used to prepare bathing, beauty or nursing preparations.

It is confirmed by clinical verification that the fatty acid composition, plant extract and pharmaceutical preparation provided by the present invention have a good effect in treating various kinds of trauma. They have the advantages of a wide scope of application, fast repair, no scab, no formation of purulent tissue, low infection rate, and no formation of scar after healing (the statistical result of clinical experiment is shown in Table 1).

TABLE 1

| Type of trauma | Degree of injury | Healing time (day) | No. of cured cases | Healing effect and remarks |
| --- | --- | --- | --- | --- |
| Wound of mechanical injury | Mild~ severe | 1-7 | 30 | No scar is formed after healing; Faster healing and better curative effect in comparison with antiphlogistine, burn cream and baiyao; |
| Burn and scald | Mild~ moderate | 1-3 | 20 | No scar is formed after healing; Faster healing and better curative effect in comparison with burn cream and baiyao; |
| Burn and scald | Severe | 10-15 | 10 | Healed; |
| Injury of chemical corrosion | Mild | 1-2 | 3 | No scar is formed after healing; Faster healing and better curative effect in comparison with burn cream and baiyao; (no moderate or severe cases are encountered) |
| Ulceration and fester | Mild~ moderate | 1-7 | 4 | No scar is formed after healing; Faster healing and better curative effect in comparison with burn cream and baiyao; (no severe cases are encountered) |
| Bedsore | Mild~ severe | 1-10 | 5 | No scar is formed after healing; Faster healing and better curative effect in comparison with antiphlogistine, burn cream and baiyao; |
| Infectious fistula | Mild~ moderate | 1-15 | 7 | No scar is formed after healing; Faster healing and better curative effect in comparison with antiphlogistine, burn cream and baiyao; (no severe cases are encountered) |

TABLE 1-continued

| Type of trauma | Degree of injury | Healing time (day) | No. of cured cases | Healing effect and remarks |
|---|---|---|---|---|
| UV radiation injury | Severe | 1-2 | 3 | No scar is formed after healing; Faster healing and better curative effect in comparison with antiphlogistine, burn cream and baiyao; |
| Serious diabetic necrosis and ulceration | Severe | 10-15 | 5 | The patients who were going to receive amputations as all treatments tried in a half year were failed were healed after they used this medicine. |

Table 1 shows the statistical data of clinical application of the plant extract, fatty acid composition and pharmaceutical preparation provided by the present invention. The plant extract, fatty acid composition and pharmaceutical preparation provided by the present invention have a very wide scope of application and may be used to treat various diseases in the departments of surgery, burn, stomatology, dermatology, plastic surgery, gynecology, otorhinolaryngology, etc., as well as to clean the wounds in outpatient department and at home. They have good repair and treatment functions to various kinds of tissue trauma. Moreover, the healing is fast, no scar is formed on wound after repair, and they may effectively prevent formation of tissue exudate, eliminate inflammation and infection induced by trauma, and can cure burn and scald of above moderate degree even without the combined use of anti-inflammatory medicines. When the pharmaceutical preparation provided by the present invention is made into cream, it may be used in dressing.

Before the present invention, it has never been recorded that the plant extract, fatty acid composition and their pharmaceutical preparation related to the present invention can be used in the foregoing usages.

Further, the inventor of the present invention has discovered during research that when any of oleic acid, linoleic acid, linolenic acid, palmitic acid, palmitoleic acid, stearic acid and arachidic acid is used alone, it also has certain curative effect as mentioned above, but the effect is relatively unobvious, while after the foregoing components are combined by the methods provided by the present invention, an obvious treatment or repair effect may be obtained. In other words, the combination of the foregoing components produces a synergistic effect.

Further, the addition of any of oleic acid, linoleic acid, linolenic acid, palmitic acid, palmitoleic acid, stearic acid, arachidic acid and docosanoic acid into the existing medicines for treatment of external trauma, medicines for treatment of burn and scald, medicines for treatment and repair of tissue ulceration or necrosis, medicines for treatment and repair of wounds, and skin care products has slight and unobvious advantage in the foregoing treatment and repair effect compared to the existing medicines or skin care products not containing the foregoing component.

The dosage of the plant extract, fatty acid composition and pharmaceutical preparation provided by the present invention has a relation with dosage form, size of wound and severity of injury. In the present invention, the dosage of a medicine refers to the dosage of the active components in the medicine.

For example, when a medicine in form of cream is used, the cream is evenly smeared on the wounded part. Typically, the dosage shall be just enough to evenly and fully cover the wound. Supposing the area of a surface wound is 20-200 $cm^2$, the dosage is about 10-100 mg/time, 1-3 times a day. When the form is aerosol, the preferred dosage of active components is 0.1-10 mg/time, 1-3 times a day. When the form is paste, the preferred content of active components on each paste is 10-100 mg, and 1-3 pastes are replaced a day. When other dosage forms for external use are used, the preferred dosage of active components is 1-100 mg/time.

When the plant extract, fatty acid composition or pharmaceutical preparation provided by the present invention is used as an internal medicine (oral administration or injection), the preferred dosage is 10-900 mg/day, such as: 100 mg/day, 200 mg/day, 300 mg/day, 400 mg/day, 500 mg/day, 600 mg/day, 700 mg/day or 800 mg/day.

Below, through examples, the present invention is described in more details.

The oleic acid, linoleic acid, linolenic acid, palmitic acid, palmitoleic acid, stearic acid, arachidic acid and docosanoic acid are all analytically pure. The *Suaeda. Salsa* (L.) Pall. was collected from coastal shoal of Qingdao.

Conditions of gas chromatography: chromatographic column: SP-2560 (100 mm×0.25 mm×0.2 m); carrier gas: high-purity helium; FID; injector temperature: 240° C.; split ratio: 50:1; stage-2 temperature programming of the column oven: the initial temperature is 165° C. and held 30 min, then the temperature is raised to 200° C. at a rate of 1.5° C./min and held 20 min, then the temperature is raised to 230° C. at a rate of 5° C./min and held 5 min. Pressure: 266.9 kPa; column flow: 1.40 mL/min; linear speed: 20 cm/s. Other conditions shall refer to Chinese national standards GB/T17376 and GB/T17377.

EXAMPLE 1

20 pbw (part by weight) of oleic acid, 79 pbw of linoleic acid and 1 pbw of linolenic acid are mixed to form fatty acid composition FA-1.

EXAMPLE 2

10 pbw of oleic acid, 70 pbw of linoleic acid and 20 pbw of linolenic acid are mixed to form fatty acid composition FA-2.

EXAMPLE 3

6 pbw of oleic acid, 85 pbw of linoleic acid and 9 pbw of linolenic acid are mixed to form fatty acid composition FA-3.

EXAMPLE 4

10 pbw of oleic acid, 75 pbw of linoleic acid, 5 pbw of linolenic acid, 1.5 pbw of palmitoleic acid, 1.5 pbw of stearic acid, 0.6 pbw of arachidic acid and 0.4 pbw of docosanoic acid are mixed to form fatty acid composition FA-4.

EXAMPLE 5

10 pbw of oleic acid, 75 pbw of linoleic acid, 5 pbw of linolenic acid, 6 pbw of palmitic acid, 1.5 pbw of stearic acid, 0.6 pbw of arachidic acid and 0.4 pbw of docosanoic acid are mixed to form fatty acid composition FA-5.

EXAMPLE 6

10 pbw of oleic acid, 75 pbw of linoleic acid, 5 pbw of linolenic acid, 6 pbw of palmitic acid, 1.5 pbw of palmitoleic acid, 0.6 pbw of arachidic acid and 0.4 pbw of docosanoic acid are mixed to form fatty acid composition FA-6.

EXAMPLE 7

10 pbw of oleic acid, 75 pbw of linoleic acid, 5 pbw of linolenic acid, 6 pbw of palmitic acid, 1.5 pbw of palmitoleic acid, 1.5 pbw of stearic acid and 0.4 pbw of docosanoic acid are mixed to form fatty acid composition FA-7.

EXAMPLE 8

10 pbw of oleic acid, 75 pbw of linoleic acid, 5 pbw of linolenic acid, 6 pbw of palmitic acid, 1.5 pbw of palmitoleic acid, 1.5 pbw of stearic acid and 0.6 pbw of arachidic acid are mixed to form fatty acid composition FA-8.

EXAMPLE 9

10 pbw of oleic acid, 75 pbw of linoleic acid, 5 pbw of linolenic acid, 6 pbw of palmitic acid, 1.5 pbw of palmitoleic acid, 1.5 pbw of stearic acid, 0.6 pbw of arachidic acid and 0.4 pbw of docosanoic acid are mixed to form fatty acid composition FA-9.

EXAMPLE 10

15 pbw of oleic acid, 73 pbw of linoleic acid, 6 pbw of linolenic acid, 4.5 pbw of palmitic acid, 0.5 pbw of palmitoleic acid, 0.7 pbw of stearic acid, 0.2 pbw of arachidic acid and 0.1 pbw of docosanoic acid are mixed to form fatty acid composition FA-10.

EXAMPLE 11

8 pbw of oleic acid, 80 pbw of linoleic acid, 2 pbw of linolenic acid, 3 pbw of palmitic acid, 3 pbw of palmitoleic acid, 2.5 pbw of stearic acid, 1 pbw of arachidic acid and 0.5 pbw of docosanoic acid are mixed to form fatty acid composition FA-11.

EXAMPLE 12

100 kg of mature seeds of *Suaeda. Salsa* (L.) Pall. are pressed by screw extrusion device to obtain 20 kg of extract EX-1.

The components of EX-1 are researched by gas chromatography. It is confirmed that EX-1 contains: 10.82 wt % oleic acid, 75.14 wt % linoleic acid, 4.53 wt % linolenic acid, 6.08 wt % palmitic acid, 1.35 wt % palmitoleic acid, 1.22 wt % stearic acid, 0.56 wt % arachidic acid and 0.28 wt % docosanoic acid based on the total amount of EX-1.

EXAMPLE 13

100 kg of mature seeds of *Suaeda. Salsa* (L.) Pall. are extracted by organic solvent leaching method to obtain 30 kg of extract EX-2. The leach liquor is 6#solvent oil and the conditions of the leaching process include: temperature 55° C., and soaking time 100 min.

The components of EX-2 are researched by gas chromatography. It is confirmed that EX-2 contains: 9.54 wt % oleic acid, 75.78 wt % linoleic acid, 4.21 wt % linolenic acid, 6.96 wt % palmitic acid, 1.15 wt % palmitoleic acid, 1.36 wt % stearic acid, 0.65 wt % arachidic acid and 0.32 wt % docosanoic acid based on the total amount of EX-2.

EXAMPLE 14

100 kg of mature seeds of *Suaeda. Salsa* (L.) Pall. are extracted by supercritical extraction method to obtain 25 kg of extract EX-3. The extractant is $CO_2$, the extraction pressure is 50 MPa, and the extraction temperature is 50° C.

The components of EX-3 are researched by gas chromatography. It is confirmed that EX-3 contains: 10.15 wt % oleic acid, 74.21 wt % linoleic acid, 4.26 wt % linolenic acid, 7.12 wt % palmitic acid, 1.58 wt % palmitoleic acid, 1.53 wt % stearic acid, 0.70 wt % arachidic acid and 0.24 wt % docosanoic acid based on the total amount of EX-3.

EXAMPLE 1 OF ANIMAL EXPERIMENT

In the model of aseptic wound of animal, 30 New Zealand white rabbits were taken and the back of each rabbit was dehaired and cut to form a 3 cm long and 0.2 cm deep wound.

Every two rabbits formed a group (parallel experiment). They were treated by smearing the foregoing medicines, 3 times a day, 100 mg a time. The rabbits in the control group were treated with Yunnan Baiyao at a same dosage by a same method. The healing time and treatment effect are shown in Table 2 below. Table 2 lists the test results of the compositions and extracts from the examples in the model of aseptic wound of animal:

TABLE 2

| Medicine | Healing time (day) | Effect |
| --- | --- | --- |
| EX-1 | 2 | No scar |
| EX-2 | 2 | No scar |
| EX-3 | 2 | No scar |
| FA-1 | 4 | Have scar |
| FA-2 | 4 | Have scar |
| FA-3 | 4 | Have scar |
| FA-4 | 3 | Unremarkable scar |
| FA-5 | 3 | Unremarkable scar |
| FA-6 | 3 | Unremarkable scar |
| FA-7 | 3 | Unremarkable scar |
| FA-8 | 3 | Unremarkable scar |
| FA-9 | 3 | No scar |
| FA-10 | 3 | No scar |
| FA-11 | 3 | No scar |
| Yunnan Baiyao (control group) | 5 | Remarkable scar |

EXAMPLE 2 OF ANIMAL EXPERIMENT

In the model of infected wound of animal: 30 New Zealand white rabbits were taken and the back of each rabbit was dehaired and cut to form a 3 cm long and 0.2 cm deep wound. The wound was smeared with an cotton swab absorbing tap water until the wound was red and swollen and purulent exudate was seen.

Every two rabbits formed a group (parallel experiment). They were treated by smearing the foregoing medicines, 3 times a day, 100 mg a time. The rabbits in the control group were treated with erythromycin ointment at a same dosage by a same method. The healing time and treatment effect are shown in Table 3 below. Table 3 lists the test results of the compositions and extracts from the examples in the model of infected wound of animal:

TABLE 3

| Medicine | Healing time (day) | Effect |
|---|---|---|
| EX-1 | 4 | No scar |
| EX-2 | 4 | No scar |
| EX-3 | 4 | No scar |
| FA-1 | 7 | Have scar |
| FA-2 | 7 | Have scar |
| FA-3 | 7 | Have scar |
| FA-4 | 6 | Unremarkable scar |
| FA-5 | 6 | Unremarkable scar |
| FA-6 | 6 | Unremarkable scar |
| FA-7 | 6 | Unremarkable scar |
| FA-8 | 5 | Unremarkable scar |
| FA-9 | 5 | No scar |
| FA-10 | 5 | No scar |
| FA-11 | 5 | No scar |
| Erythromycin ointment (control group) | 8 | Remarkable scar |

EXAMPLE 3 OF ANIMAL EXPERIMENT

In the model of burn wound of animal, 30 New Zealand white rabbits were taken and a cotton ball was ignited to burn the skin of rabbit back until the skin was charred and the wound was red and swollen.

Every two rabbits formed a group (parallel experiment). They were treated by smearing the foregoing medicines, 3 times a day, 100 mg a time. The rabbits in the control group were treated with moist exposed burn ointment (MEBO) at a same dosage by a same method. The healing time and treatment effect are shown in Table 4 below. Table 4 lists the test results of the compositions and extracts from the examples in the model of burn wound of animal:

TABLE 4

| Medicine | Healing time (day) | Effect |
|---|---|---|
| EX-1 | 5 | No scar |
| EX-2 | 5 | No scar |
| EX-3 | 5 | No scar |
| FA-1 | 9 | Have scar |
| FA-2 | 9 | Have scar |
| FA-3 | 9 | Have scar |
| FA-4 | 8 | Unremarkable scar |
| FA-5 | 8 | Unremarkable scar |
| FA-6 | 7 | Unremarkable scar |
| FA-7 | 8 | Unremarkable scar |
| FA-8 | 7 | Unremarkable scar |
| FA-9 | 6 | No scar |
| FA-10 | 6 | No scar |
| FA-11 | 6 | No scar |
| MEBO (control group) | 10 | Remarkable scar |

EXAMPLE 4 OF ANIMAL EXPERIMENT

In the model of animal wound caused by corrosion of strong acid, 30 New Zealand white rabbits were taken and a cotton ball soaked with concentrated sulfuric acid was used to smear the skin of rabbit back until the skin was corroded and injured and the wound was red, swollen and festered. Every two rabbits formed a group (parallel experiment). They were treated by smearing the foregoing medicines, 3 times a day, 100 mg a time. The rabbits in the control group were treated with moist exposed burn ointment (MEBO) at a same dosage by a same method. The healing time and treatment effect are shown in Table 5 below. Table 5 lists the test results of the compositions and extracts from the examples in the model of animal wound caused by corrosion of strong acid:

TABLE 5

| Medicine | Healing time (day) | Effect |
|---|---|---|
| EX-1 | 10 | No scar |
| EX-2 | 10 | No scar |
| EX-3 | 10 | No scar |
| FA-1 | 14 | Have scar |
| FA-2 | 14 | Have scar |
| FA-3 | 14 | Have scar |
| FA-4 | 13 | Unremarkable scar |
| FA-5 | 12 | Unremarkable scar |
| FA-6 | 13 | Unremarkable scar |
| FA-7 | 12 | Unremarkable scar |
| FA-8 | 13 | Unremarkable scar |
| FA-9 | 11 | No scar |
| FA-10 | 11 | No scar |
| FA-11 | 11 | No scar |
| MEBO (control group) | 15 | Remarkable scar |

EXAMPLE 5 OF ANIMAL EXPERIMENT

In the model of animal wound caused by corrosion of strong alkali, 30 New Zealand white rabbits were taken and a cotton ball soaked with 10 wt % NaOH was used to smear the skin of rabbit back until the skin was corroded and injured and the wound was red and swollen.

Every two rabbits formed a group (parallel experiment). They were treated by smearing the foregoing medicines, 3 times a day, 100 mg a time. The rabbits in the control group were treated with moist exposed burn ointment (MEBO) at a same dosage by a same method. The healing time and treatment effect are shown in Table 6 below. Table 6 lists the test results of the compositions and extracts from the examples in the model of animal wound caused by corrosion of strong alkali:

TABLE 6

| Medicine | Healing time (day) | Effect |
|---|---|---|
| EX-1 | 6 | No scar |
| EX-2 | 6 | No scar |
| EX-3 | 6 | No scar |
| FA-1 | 12 | Have scar |
| FA-2 | 12 | Have scar |
| FA-3 | 12 | Have scar |
| FA-4 | 10 | Unremarkable scar |
| FA-5 | 11 | Unremarkable scar |
| FA-6 | 10 | Unremarkable scar |
| FA-7 | 9 | Unremarkable scar |

TABLE 6-continued

| Medicine | Healing time (day) | Effect |
|---|---|---|
| FA-8 | 8 | Unremarkable scar |
| FA-9 | 7 | No scar |
| FA-10 | 7 | No scar |
| FA-11 | 7 | No scar |
| MEBO (control group) | 13 | Remarkable scar |

EXAMPLE 1 OF CLINICAL TEST

Patient: Male, 97.

Symptom: The patient fell on a stone step, resulting in about 5×3 cm of damage of the skin in front of patella. As there is little muscle at patella and blood supply is poor, and it was hot in August and the patient smeared anti-inflammatory medicine by himself, purulence and ulceration deep to the patella appeared at the damaged skin two days later.

Treatment: EX-1 was directly smeared three times a day, 300 mg a time. After three days, ulcer and purulent secretion decreased, peripheral skin grew towards the center and the wound shrank. As the patient's family was eager for treatment, they used MEBO and stopped the use of EX-1. When they saw the skin around the wound turned white and the wound was worsened, they used EX-1 again two days later. As a result, the wound shrank. After ten days, the wound was completely healed and no scar was left.

EXAMPLE 2 OF CLINICAL TEST

Patient: Male, 18.

Symptom: A forefinger of the patient was cut by a cutter during construction, leaving a 1 cm long, 0.5 cm wide and 3 mm deep missing wound.

Treatment: After bleeding was stopped, EX-1 was smeared, 3 times a day, 100 mg a time. The wound was healed after three days and became as usual skin after seven days.

EXAMPLE 3 OF CLINICAL TEST

Patient: Male, 52.

Symptom: During morning exercise, his hair line was scratched by a tree branch.

The wound was irregular, about 1 cm long and 0.3 cm deep.

Treatment: After bleeding was stopped, EX-1 was smeared, 3 times a day, 100 mg a time. The wound was healed after three days and no scar was left.

EXAMPLE 4 OF CLINICAL TEST

Patient: Female, 18.

Symptom: The back of her right hand was scratched. The wound was irregular, about 3.3 cm long and 2.6 cm wide, with an irregular edge.

Treatment: EX-1 was applied, twice a day, 100 mg a time. The wound was not infected. After two days, it was healed and no scar was left.

EXAMPLE 5 OF CLINICAL TEST

Patient: Male, 7.

Symptom: The forehead was injured after a knock. The wound was irregular, about 3 cm×3 cm, with an irregular edge.

Treatment: 100 mg of EX-1 was smeared directly. The wound was not infected.

After one day, it was healed and no scar was left.

EXAMPLE 6 OF CLINICAL TEST

Patient: Female, 45.

Symptom: The palm of her left hand was scalded in an oil pot. The wound was irregular, about 5 cm×10 cm, red, swollen and blistered.

Treatment: EX-1 was smeared, three times a day, 300 mg a time. The wound was not infected. After three days, it was healed and no scar was left.

EXAMPLE 7 OF CLINICAL TEST

Patient: Male, 30, a chef.

Symptom: The back of his hand was injured by burn during cooking. The wound was irregular, 5 cm×6 cm, red, swollen and blistered.

Treatment: EX-1 was smeared, three times a day, 200 mg a time. The wound was not infected. After two days, it was healed and no scar was left.

EXAMPLE 8 OF CLINICAL TEST

Patient: Male, 50, a scientific researcher.

Symptom: Cheek skin was burnt by sulfuric acid during experiment. The wound was irregular, about 1 cm×2 cm, incomplete due to corrosion, red and swollen.

Treatment: After water washing, EX-1 was smeared, three times a day, 100 mg a time.

The wound was not infected. After two days, it was healed and no scar was left.

EXAMPLE 9 OF CLINICAL TEST

Patient: Male, 83.

Symptom: The patient suffered diabetes and was hospitalized due to hemiplegia. Oppressed ulceration appeared on a foot. The wound was irregular, about 2 cm×4 cm.

The bedsore on buttock was round, about 3 cm×3 cm.

Treatment: EX-1 was smeared, three times a day, 100 mg a time for the foot and 200 mg a time for the buttock. Bedsore was healed after five days and the ulceration on the foot was healed after seven days.

EXAMPLE 10 OF CLINICAL TEST

Patient: Male, 45.

Symptom: The patient had infectious flu. The corners of his mouth were ulcerated, blistered and infected.

Treatment: EX-1 was smeared, three times a day, 100 mg a time. After three days, the wound was healed and no scar was left.

EXAMPLE 11 OF CLINICAL TEST

Patient: Female, 20.

Symptom: The patient was exposed under the scorching sun in summer too long and the skin on face and body was radiated by UV light. Consequently, the skin was red, swollen, burnt and painful in a large area.

Treatment: 600 mg of EX-1 was applied. The pain was stopped immediately. EX-1 was smeared three times a day, 600 mg a time. After two days, the wound was healed and no scar was left.

EXAMPLE 12 of Clinical Test

Patient: Female, 30.

Symptom: The skin was dry. Fingers were chapped and painful at multiple points.

Treatment: 100 mg of EX-1 was applied. The pain was stopped immediately. EX-1 was smeared three times a day, 100 mg a time. After two days, the wound was healed, no scar was left and the skin was fine and smooth.

EXAMPLE 13 of Clinical Test

Patient: Male, 5.

Symptom: After intramuscular injection, the damage caused by needle turned red and became swollen and was painful.

Treatment: 50 mg of EX-11 was applied. The pain was stopped immediately. After one day, swelling disappeared and the wound was healed.

What is claimed is:

1. A method of treating a rupture injury, burn injury, scald injury ,tissue ulceration, electric injury, radiational injury causing burn and scald injury, chemical corrosive injury, intractable ulcer caused by diabetes or varicosity, gangrene wound, bedsore, ulceration, or bleeding of the alimentary tract in a human or animal in need thereof comprising administering to said human or animal in need thereof a therapeutically effective amount of an extract of *Suaeda* seeds, wherein said rupture injury, burn injury, scald injury, tissue ulceration, electric injury, radiational injury causing burn and scald injury, chemical corrosive injury, intractable ulcer caused by diabetes or varicosity, gangrene wound, bedsore, ulceration, or bleeding of alimentary tract, in the human or animal in need thereof is effectively treated.

2. The method according to claim 1, wherein the extract of *Suaeda* seeds comprises oleic acid, linoleic acid, and linolenic acid and based on the weight of the extract of *Suaeda* seeds, the content of the oleic acid is 0.5-99 wt %, the content of the linoleic acid is 0.5-99 wt % and the content of linolenic acid is 0.5-99 wt %.

3. The method according to claim 2, wherein based on the weight of the extract of *Suaeda* seeds, the content of the oleic acid is 5-30 wt %, the content of the linoleic acid is 60-90 wt %, and the content of the linolenic acid is 0.5-30 wt %.

4. The method according to claim 2, wherein based on the weight of the extract of *Suaeda* seeds, the content of oleic acid is 6-20 wt %, the content of linoleic acid is 70-85 wt %, and the content of linolenic acid is 1-20 wt %.

5. The method according to claim 1, wherein the extract of *Suaeda* seeds comprises oleic acid, linoleic acid, linolenic acid, palmitic acid, palmitoleic acid, stearic acid, arachidic acid and docosanoic acid.

6. The method according to claim 1, wherein the extract of *Suaeda* seeds comprises oleic acid, linoleic acid, linolenic acid, palmitic acid, palmitoleic acid, stearic acid, arachidic acid, and dosanoic acid, and based on the weight of the extract of *Suaeda* seeds, the content of the oleic acid is 0.5-95 wt %, the content of the linoleic acid is 0.5-95 wt %, the content of the linolenic acid is 0.5-95 wt %, the content of the palmitic acid is 0-8 wt %, the content of the palmitoleic acid is 0-3 wt %, the content of the stearic acid is 0-3 wt %, the content of the arachidic acid is 0-1 wt % and the content of the docosanoic acid is 0-1 wt %.

7. The method according to claim 6, wherein based on the weight of the extract of *Suaeda* seeds, the content of the oleic acid is 6-20 wt %.

8. The method according to claim 6, wherein based on the weight of the extract of *Suaeda* seeds, the content of oleic acid is 8-15 wt %.

9. The method according to claim 6, wherein based on the weight of the extract of *Suaeda* seeds, the content of the linoleic acid is 70-85 wt %.

10. The method according to claim 6, wherein based on the weight of the extract of *Suaeda* seeds, the content of the linoleic acid is 72-80 wt %.

11. The method according to claim 6, wherein based on the weight of the extract of *Suaeda* seeds, the content of linolenic acid is 1-20 wt %.

12. The method according to claim 6, wherein based on the weight of the extract of *Suaeda* seeds, the content of linolenic acid is 2-6 wt %.

13. The method according to claim 6, wherein the *Suaeda* is selected from the group consisting of *Suaeda*. Salsa (L.) Pall., *S. glauca* Bge., *S. corniculata* (C.A.Mey) Bunge, *S. prostrata* Pall, and combinations thereof.

14. The method according to claim 13, wherein the extract of *Suaeda* seeds is prepared by a method selected from the group consisting of a compression method, a leaching method, a supercritical extraction method, a water extraction method, and combinations thereof;
　　wherein the compression method is achieved by directly extruding lipid from the *Suaeda* seeds using an oil press;
　　wherein the leaching method uses a leach liquor containing a solvent with a boiling point of 40-90° C.; and
　　wherein the supercritical extraction method uses an extractant selected from the group consisting of carbon dioxide, ethylene, ammonia, nitrous oxide, dichlorodifluoromethane, and combinations thereof.

15. The method according to claim 14, wherein the leach liquor is selected from the group consisting of n-hexane, benzene, dichloroethane, trichloroethylene, gasoline, and combinations thereof.

16. The method according to claim 1, wherein the extract of *Suaeda* seeds is in the form of a skin-protecting agent, and wherein the skin-protecting agent is selected from the group consisting of sunscreens, anti-chapping preparations, skin moisturizing preparations, bathing preparations, beauty preparations and nursing preparations.

17. The method according to claim 1, wherein the extract of *Suaeda* seeds further comprises one or more of pharmaceutical adjuvants and other pharmaceuticals adjuvants.

18. The method according to claim 1, wherein the extract of *Suaeda* seeds is in a form selected from the group consisting of a liniment, a cream, a paste, a suppository, a hard capsule, a soft capsule, an aerosol, a solution, an emulsion, a dispersant, a tablet, a pill, a film and an injection.

19. The method of claim 1, wherein the extract of *Suaeda* seeds is a fatty acid extract of *Suaeda* seeds or a lipid extract of *Suaeda* seeds.

* * * * *

UNITED STATES PATENT AND TRADEMARK OFFICE
CERTIFICATE OF CORRECTION

| | | |
|---|---|---|
| PATENT NO. | : 9,446,083 B2 | Page 1 of 1 |
| APPLICATION NO. | : 14/129803 | |
| DATED | : September 20, 2016 | |
| INVENTOR(S) | : Xing et al. | |

It is certified that error appears in the above-identified patent and that said Letters Patent is hereby corrected as shown below:

In the Specification

In Column 19 at Line 29, change "injury ,tissue" to -- injury, tissue --

In the Claims

In Column 20 at Line 56, delete the second occurrence of "adjuvants"

Signed and Sealed this
Thirtieth Day of May, 2017

Michelle K. Lee
*Director of the United States Patent and Trademark Office*